United States Patent
Ilias et al.

(10) Patent No.: US 11,203,557 B2
(45) Date of Patent: Dec. 21, 2021

(54) CATALYST AND ITS USE IN DEHYDROCYCLIZATION PROCESSES

(71) Applicant: ExxonMobil Chemical Patents Inc., Baytown, TX (US)

(72) Inventors: Samia Ilias, Somerville, NJ (US); Mayank Shekhar, Houston, TX (US); Paul F. Keusenkothen, Houston, TX (US); John S. Buchanan, Flemington, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/240,707

(22) Filed: Aug. 18, 2016

(65) Prior Publication Data

US 2017/0087540 A1    Mar. 30, 2017

Related U.S. Application Data

(60) Provisional application No. 62/232,609, filed on Sep. 25, 2015.

(30) Foreign Application Priority Data

Nov. 19, 2015 (EP) .................... 15195311

(51) Int. Cl.
| | |
|---|---|
| C07C 2/76 | (2006.01) |
| B01J 29/40 | (2006.01) |
| B01J 29/064 | (2006.01) |
| B01J 19/24 | (2006.01) |
| F02C 3/22 | (2006.01) |
| C07C 5/41 | (2006.01) |
| B01J 37/28 | (2006.01) |

(52) U.S. Cl.
CPC ............. *C07C 2/76* (2013.01); *B01J 19/24* (2013.01); *B01J 29/064* (2013.01); *B01J 29/40* (2013.01); *B01J 29/405* (2013.01); *C07C 5/415* (2013.01); *F02C 3/22* (2013.01); *B01J 37/28* (2013.01); *B01J 2219/00103* (2013.01); *B01J 2229/186* (2013.01); *C07C 2529/40* (2013.01); *F05D 2220/32* (2013.01); *F05D 2220/76* (2013.01)

(58) Field of Classification Search
None
See application file for complete search history.

(56) References Cited

U.S. PATENT DOCUMENTS

| | | | | |
|---|---|---|---|---|
| 4,665,251 A | * | 5/1987 | Chu .................. | B01J 29/40 585/415 |
| 4,855,522 A | * | 8/1989 | Diaz .................. | C07C 2/00 585/417 |
| 5,026,937 A | * | 6/1991 | Bricker ............... | C07C 2/76 585/415 |

(Continued)

*Primary Examiner* — Tam M Nguyen

(57) ABSTRACT

The invention relates to catalysts and their use in processes for dehydrocyclization of light paraffinic hydrocarbon feedstock to higher-value hydrocarbon, such as aromatic hydrocarbon, to dehydrocyclization catalysts useful in such processes, and to the methods of making such catalysts. One of more of the dehydrocyclization catalysts comprising a crystalline aluminosilicate zeolite having a constraint index of less than or equal to about 12, at least one Group 3 to Group 13 metal of the IUPAC Periodic Table and phosphorous.

24 Claims, 3 Drawing Sheets

(▲) C1-with 1 wt% phosphorous
(●) D1-on H-ZSM-5 containing 1.5 wt% Gallium

(▲) C1-with 1 wt% phosphorous
(●) D1-on H-ZSM-5 containing 1.5 wt% Gallium

(56) References Cited

U.S. PATENT DOCUMENTS

| | | | |
|---|---|---|---|
| 5,936,135 A * | 8/1999 | Choudhary | C07C 2/00 585/418 |
| 5,990,032 A * | 11/1999 | Wu | B01J 29/061 502/60 |
| 7,589,246 B2 * | 9/2009 | Iaccino | B01J 29/90 585/407 |
| 7,795,490 B2 * | 9/2010 | Iaccino | C07C 2/76 585/415 |
| 8,841,227 B2 * | 9/2014 | Sangar | B01J 35/0006 502/77 |
| 9,144,790 B2 * | 9/2015 | Lauritzen | C10G 45/70 |
| 9,796,643 B2 * | 10/2017 | Buchanan | B01J 29/7861 |
| 9,815,749 B2 * | 11/2017 | Keusenkothen | B01J 29/7876 |
| 9,988,325 B2 * | 6/2018 | Keusenkothen | C10G 11/00 |
| 10,071,938 B2 * | 9/2018 | Shekhar | B01J 29/44 |
| 10,273,196 B2 * | 4/2019 | Keusenkothen | B01J 8/067 |
| 2004/0192990 A1 * | 9/2004 | Choudhary | C07C 1/20 585/638 |
| 2010/0185034 A1 * | 7/2010 | Nishimura | B01J 29/7876 585/420 |
| 2017/0088488 A1 * | 3/2017 | Shekhar | B01J 35/023 |
| 2017/0305812 A1 * | 10/2017 | Keusenkothen | B01J 29/061 |
| 2018/0022667 A1 * | 1/2018 | Buchanan | C07C 9/04 518/702 |

\* cited by examiner

(▲) A2-without addition of phosphorous
(■) A1-with addition of phosphorous

FIG. 1A

(▲) B2-without addition of phosphorous
(■) B1-with addition of phosphorous

FIG. 1B

(▲) C2-without addition of phosphorous
(■) C1-with addition of phosphorous

(▲) C1-with 1 wt% phosphorous
(●) D1-on H-ZSM-5 containing 1.5 wt% Gallium

FIG. 3A

(▲) C1-with 1 wt% phosphorous
(●) D1-on H-ZSM-5 containing 1.5 wt% Gallium

FIG. 3B

(▲) C1-with 1 wt% phosphorous
(●) D1-on H-ZSM-5 containing 1.5 wt% Gallium

FIG. 3C

CATALYST AND ITS USE IN DEHYDROCYCLIZATION PROCESSES

CROSS REFERENCE TO RELATED APPLICATIONS

This invention claims priority to and the benefit of U.S. patent application Ser. No. 62/232,609 filed Sep. 25, 2015, and European Patent Application No. 15195311.4 filed Nov. 19, 2015, both of which are incorporated by reference in their entireties. The following related cases are also incorporated by reference in their entireties: U.S. patent application Ser. No. 62/234,262; European Patent Application No. 15195314.8; U.S. patent application Ser. No. 62/234,240; European Patent Application No. 15197698.2; U.S. patent application Ser. No. 62/247,795; European Patent Application No. 15197700.6; U.S. patent application Ser. No. 62/248,374; European Patent Application No. 15197702.2; U.S. patent application Ser. No. 62/253,268; U.S. patent application Ser. No. 62/298,655; European Patent Application No. 16167672.1; U.S. patent application Ser. No. 62/326,918; European Patent Application No. 16175163.1; U.S. patent application Ser. No. 62/299,730; European Patent Application No. 16167395.9; U.S. patent application Ser. No. 62/313,288; European Patent Application No. 16173587.3; U.S. patent application Ser. No. 62/313,306, European Patent Application No. 16173980.0, and U.S. patent application Ser. No. 62/327,023 filed Apr. 25, 2016.

FIELD

The invention relates to catalysts and their use in processes for dehydrocyclization of a light paraffinic hydrocarbon feedstock to a product of higher-value hydrocarbon. Preferably, the light paraffinic hydrocarbon feedstock comprises one or more light hydrocarbons having no more than five carbons atoms, such as for example, methane, ethane, propane or butane. The higher-value hydrocarbon is preferably aromatic hydrocarbon having six or more carbon atoms, for example, benzene, toluene and mixed xylenes.

BACKGROUND

Aromatic hydrocarbon compounds such as benzene are frequently used for producing transportation fuels and petrochemicals such as styrene, phenol, nylon and polyurethanes and many others. Benzene is typically produced in processes such as steam cracking and catalytic reforming. During steam cracking, a $C_{2+}$ hydrocarbon feedstock is exposed to high-temperature pyrolysis conditions to produce a product comprising molecular hydrogen, $C_{4-}$ olefin, other $C_{4-}$ hydrocarbon, and $C_{5+}$ hydrocarbon. The yield of aromatic hydrocarbon from steam cracking is generally much less than the yield of light hydrocarbon. Consequently, complex processes typically are needed for separating and recovering aromatic hydrocarbon from steam cracker effluent. Catalytic naphtha reforming produces a product having a much greater content of aromatic hydrocarbon than steam cracker effluent, but the naphtha feedstock is itself useful for other purposes such as a motor gasoline blendstock.

Various attempts have been made to provide an efficient process for producing aromatic hydrocarbon at high yield from a relatively inexpensive feedstock. For example, processes have been developed for producing light aromatic hydrocarbon (e.g., benzene, toluene, and mixed xylenes—"BTX") from paraffinic $C_{4-}$ feedstock. The processes typically utilize an acidic molecular sieve such as ZSM-5 and at least one metal having dehydrogenation functionality, such as one or more of Pt, Ga, Zn, and Mo. These conventional processes typically operate at high temperature and low pressure. Although these conditions are desirable for producing aromatic hydrocarbon, they also lead to undue catalyst deactivation as a result of increased catalyst coking. Catalyst coking generally worsens under conditions which increase feedstock conversion, leading to additional operating difficulties.

One way to lessen the amount of catalyst coking is disclosed in U.S. Pat. No. 5,026,937. The reference discloses removing $C_{2+}$ hydrocarbon from the feedstock in order to increase the feedstock's methane concentration. Since ethane, propane, and butanes are less refractory, removing these compounds from the feedstock decreases the amount of over-cracking, and lessens the accumulation of catalyst coke. The process utilizes a catalyst comprising molecular sieve, an amorphous phosphorous-modified alumina, and at least one dehydrogenation metal selected from Ga, Pt, Rh, Ru, and Ir. The catalyst contains ≤0.1 wt. % of Ni, Fe, Co, Group VIb metals, and Group VIIb metals. The reference also discloses increasing aromatic hydrocarbon yield by removing hydrogen from the reaction, e.g., by combusting the hydrogen with oxygen in the presence of an oxidation catalyst that has greater selectivity for hydrogen combustion over methane combustion.

Processes have also been developed for converting less-refractory paraffinic hydrocarbon to aromatic hydrocarbon with decreased selectivity for catalyst coke. For example, U.S. Pat. No. 4,855,522 discloses converting $C_2$, $C_3$, and $C_4$ hydrocarbon with increased selectivity for aromatic hydrocarbon and decreased selectivity for catalyst coke. The process utilizes a dehydrocyclization catalyst comprising (a) an aluminosilicate zeolite having a silica-to-alumina ($SiO_2$: $Al_2O_3$) molar ratio of at least 5 and (b) a compound of (i) Ga and (ii) at least one rare earth metal. The reference discloses carrying out the aromatization conversion at a space velocity (LHSV) in the range of from 0.5 to 8 $hr^{-1}$, a temperature ≥450° C. (e.g., 475° C. to 650° C.), a pressure of from 1 bar to 20 bar, and a feedstock contact time of 1 to 50 seconds. See also, U.S. Pat. No. 4,788,364.

More recently, catalysts have been developed to further reduce the amount of catalyst coking during the dehydrocyclization of $C_{4-}$ paraffinic hydrocarbon. For example, increasing the catalyst's dehydrogenation metal loading has been observed to lessen the amount of catalyst coking. See, e.g., U.S. Pat. No. 7,186,871. But increasing dehydrogenation metal loading has been found to increase the catalyst's hydrogenolysis activity, resulting in an increase in the amount of methane and other light saturated hydrocarbon in the reaction product and a decrease in the amount of the desired aromatic hydrocarbon. This effect may be mitigated by further increasing catalyst complexity, e.g., by adding an attenuating metal to the catalyst as disclosed in U.S. Pat. No. 8,692,043. See also, U.S. Pat. No. 8,772,563.

The addition of phosphorus to zeolites, such as ZSM-5, has been shown to be effective for the conversion of aliphatic compounds, particularly to aromatics. These phosphorous-containing zeolites may be further impregnated with zinc to increase the activity of such catalyst so that they may be more effective at lower temperatures. See U.S. Pat. Nos. 3,972,832, 4,044,065; and 6,074,975.

Therefore, processes and catalysts are needed for dehydrocyclization of light $C_{5-}$ hydrocarbon that exhibits a high feedstock conversion, a greater yield of aromatic hydrocarbon, and a lesser yield of catalyst coke and $C_{4-}$ hydrocarbon, particularly processes which may be carried out with catalysts of lesser complexity.

SUMMARY

In one aspect, the invention is a catalyst which can be used for the dehydrocyclization of a light paraffinic hydrocarbon feedstock to form aromatic hydrocarbon, preferably single-ring aromatic hydrocarbon, said catalyst comprising a crystalline aluminosilicate zeolite, optionally in hydrogen form having hydrogen ions, and a constraint index of less than or equal to about 12, at least one metal selected from Group 3 to Group 13 of the Periodic Table, preferably at least about 0.005 wt. % of said metal, and added phosphorous, preferably at least about 0.005 wt. % of phosphorous. In one or more embodiments, said catalyst is used in a dehydrocyclization process which provides one or more of (i) a yield of single-ring aromatic hydrocarbon of over 20%, preferably over 25%; and (ii) a yield of coke formed on the catalyst of less than 10%, preferably less than 5%, under dehydrocyclization conditions which include at least a temperature in the range of about 450° C. to about 650° C., a pressure in the range of from about 35 kPa to about 1480 kPa and a WHSV from 0.1 to 20 $hr^{-1}$. In one or more embodiments, said process comprising the steps of contacting said light paraffinic hydrocarbon feedstock under suitable dehydrocyclization conditions in the presence of any one of said catalysts of this invention to form said product.

In another aspect, the invention is a catalyst for the dehydrocyclization of a light paraffinic hydrocarbon feedstock comprising light $C_{5-}$ hydrocarbon to form single-ring aromatic hydrocarbon, said catalyst having phosphorous deposited upon at least one catalyst precursor. This catalyst is made by the method comprising the steps of: (a) contacting a crystalline aluminosilicate zeolite in hydrogen form having hydrogen ions and a constraint index of less than or equal to about 12 with a source of at least one metal selected from Groups 3 to 13 of the IUPAC Periodic Table, to form said catalyst precursor comprising said aluminosilicate zeolite and having at least about 0.005 wt. % of said metal; and (b) then contacting said catalyst precursor of step (a) with a source of phosphorus, whereby at least about 0.005 wt. % of phosphorus is deposited on the catalyst precursor, or deposited in or proximate to the catalyst precursor, to form said catalyst. The invention also includes dehydrocyclization processes using the catalysts of any of the foregoing embodiments.

DETAILED DESCRIPTION

The catalyst of this invention is suitably employed in a process for dehydrocyclization of light paraffinic hydrocarbon, such as natural gas feedstock, to form aromatic hydrocarbon, e.g., single-ring aromatic hydrocarbon such as benzene, toluene and/or xylenes. The natural gas feedstock comprise light hydrocarbon, such as for example, light alkanes ($C_{5-}$) or light paraffins. The process includes dehydrocyclization of at least a portion of the light paraffinic hydrocarbon feedstock's light hydrocarbon, in some embodiments in a first stage reaction, to produce a product comprising aromatic hydrocarbon, non-aromatic hydrocarbon, molecular hydrogen, and unconverted light paraffinic hydrocarbon feedstock.

It has been found that metal-containing zeolite-based catalysts used in a dehydrocyclization process of light paraffinic hydrocarbon feedstock are stabilized by the addition of phosphorus in a reducing environment. Such stabilization results in lower amounts of coke being deposited on the catalyst, thereby enabling longer catalyst cycle lengths and higher yields of desired products.

Definitions

For the purpose of this specification and appended claims, the following terms are defined.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The terms "alkane" and "paraffinic hydrocarbon" means substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes.

The terms "unsaturate" and "unsaturated hydrocarbon" refer to one or more $C_{2+}$ hydrocarbon compounds which contain at least one carbon atom directly bound to another carbon atom by a double or triple bond.

The terms "aromatics" and "aromatic hydrocarbon" mean a class of hydrocarbon compounds containing at least one aromatic core.

As used herein, the term "dehydrocyclization" means the formation of an unsaturated cyclic compound, preferably a substituted or unsubstituted aromatic compound, for example, benzene or toluene or xylene isomers, from a saturated aliphatic compound, for example, ethane, n-pentane or n-butane, or from a unsaturated aliphatic compound such as ethylene, propylene or butylene.

The term "IUPAC Periodic Table" means the IUPAC Periodic Table of the Elements, dated 1 May 2013.

The term "naphtha" means a mixture of aromatic hydrocarbon having six or more carbon atoms, also referred to as a $C_{6+}$ aromatic hydrocarbon, such as, for example, a mixed xylene.

The term "reaction zone" or "reactor zone" mean a location within a reactor, e.g., a specific volume within a reactor, for carrying out a specified reaction. A reactor or reaction stage may encompass one or more reaction zones. More than one reaction may be carried out in a reactor, reactor stage, or reaction zone.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

The term "constraint index" is defined in U.S. Pat. Nos. 3,972,832 and 4,016,218, both of which are incorporated herein by reference.

The term "yield" refers to the production of a specified compound or a class of compounds in a catalytic reaction. The phrase "a yield of single-ring aromatic hydrocarbon of over 20 wt. %" means that over 20% by weight of the light paraffinic hydrocarbon feedstock is converted to single-ring aromatic hydrocarbon under specified dehydrocyclization conditions. The phrase "a yield of coke of less than 5%" means that less than 5% by weight of the light paraffinic hydrocarbon feedstock is converted to coke under specified dehydrocyclization conditions.

The term "conversion" when used in connection with a specified reactant means the amount of the reactant consumed in the reaction. For example, when the specified reactant is propane ($C_3$) hydrocarbon, 100% conversion means 100% of the $C_3$ hydrocarbon is consumed in the reaction.

The term "weight hourly space velocity", referred to as "WHSV", means the quotient of the mass flow rate of the reactants divided by the mass of the catalyst in the reactor.

The invention includes reacting a feedstock, such as light paraffinic hydrocarbon feedstock comprising light hydrocarbon, such as light paraffinic hydrocarbon, in one or more stages to selectively convert at least a portion of the feedstock to heavier hydrocarbon, such as aromatic hydrocarbon. Representative feedstock will now be described in more detail. The invention is not limited to these feedstock, and this description is not meant to foreclose other feedstock within the broader scope of the invention.

Feedstock

The feedstock typically comprises one or more $C_2$ to $C_9$ hydrocarbon compounds, e.g., one or more light hydrocarbon (i.e., $C_2$ to $C_5$) compounds. For example, the feedstock can comprise ≥1 wt. % of light hydrocarbon based on the weight of the feed, such as ≥10 wt. %, or ≥25 wt. %, or ≥50 wt. %, or ≥75 wt. %, or ≥90 wt. %, or ≥95 wt. %. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified catalyst, e.g., methane, molecular nitrogen, and inert atomic gasses such as argon.

The feedstock typically contains $C_3$ and/or $C_4$ hydrocarbon e.g., (i) ≥20 wt. % propane, such as ≥40 wt. %, or ≥60 wt. %, and/or (ii) ≥20 wt. % butanes, such as ≥40 wt. %, or ≥60 wt. %. Although the feedstock may contain $C_5$ hydrocarbon, the amount of $C_5$ hydrocarbon when present is typically small, e.g., ≤20 wt. %, such as ≤10 wt. %, or ≤1 wt. %. Typically, the feedstock contains ≤10 wt. % of $C_{6+}$ saturated hydrocarbon, e.g., ≤5 wt. %, or ≤1 wt. %.

The feedstock may contain methane (a $C_1$ hydrocarbon), e.g., ≥1 wt. % methane, such as ≥10 wt. %, or ≥20 wt. %, or ≥30 wt. %. Even though methane is a diluent, i.e., it does not typically react to produce aromatic hydrocarbon or catalyst coke in the presence of the specified dehydrocyclization catalyst under the specified reaction conditions, its presence may be beneficial for decreasing the partial pressure of $C_2$ to $C_5$ hydrocarbon. Decreasing the partial pressure of $C_2$ to $C_5$ hydrocarbon in the feedstock has been found to lessen the amount of catalyst coke formed under the reaction conditions specified for feedstock conversion to aromatic hydrocarbon. Typically, the feedstock comprises a total of ≤10 wt. % of impurities such as CO, $CO_2$, $H_2S$, and mercaptan; e.g., ≤1 wt. %, or ≤0.1 wt. %.

Optionally, the feedstock contains unsaturated $C_{2+}$ hydrocarbon, such as one or more $C_2$-$C_5$ unsaturated hydrocarbon compounds. When present, the amount of $C_{2+}$ unsaturated hydrocarbon is typically ≤20 wt. %, e.g., ≤10 wt. %, such as ≤1 wt. %, or ≤0.1 wt. %, or in the range of from 0.1 wt. % to 10 wt. %. More particularly, the feedstock is generally one that is substantially-free of aromatic hydrocarbon, where substantially-free in this context means an aromatic hydrocarbon content that is <1 wt. % based on the weight of the feedstock, such as ≤0.1 wt. %, or ≤0.01 wt. %, or ≤0.001 wt. %.

The feedstock's light hydrocarbon may be obtained from one or more sources of hydrocarbon, e.g., from natural hydrocarbon sources such as those associated with producing petroleum, or from one or more synthetic hydrocarbon sources such as catalytic and non-catalytic reactions. Examples of such reactions include, catalytic cracking, catalytic reforming, coking, steam cracking, etc. Synthetic hydrocarbon sources include those in which hydrocarbon within a geological formation has been purposefully subjected to one or more chemical transformations. The feed can include recycle components, e.g., portions of the first and/or second product, such as portions of the first and/or second raffinate. Such recycle, when used, can include, e.g., methane, molecular hydrogen, and $C_{2+}$ hydrocarbon, typically $C_2$ to $C_5$ hydrocarbon.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional productions methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |

TABLE 1-continued

| Component | Associated Gas | Dry Gas | Condensate Well Gas |
|---|---|---|---|
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.01-1 (0.09) |

In certain aspects, the feed comprises ≥75 wt. % Associated Gas, based on the weight of the feed, e.g., ≥90 wt. %, or ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, typically results in Associated Gas being stranded at or near the reservoir. This in turn can lead to undesirable natural gas flaring. Moreover, even in locations where pipeline facilities are available, Associated Gas may be excluded from the pipeline because it typically exceeds one or more of the following typical pipeline specifications: ≤12 wt. % ethane, ≤5 wt. % propane, ≤2 wt. % butanes, a Wobbe Index of from 49.01 $MJ/sm^3$ to 52.22 $MJ/sm^3$, and a heating value of from 36.07 $MJ/sm^3$ to 41.40 $MJ/sm^3$.

Since methane is not detrimental to the process, and is in at least some aspects beneficial, the invention obviates the need for costly and inefficient cryogenic methane separation facilities, such as one or more conventional cold boxes. Typically, obtaining the feed from the source material (e.g., natural gas, such as raw gas) does not include (i) exposing the feed, source material, or any intermediate thereof to a temperature ≤−37° C., e.g., ≤−46° C., such as ≤−60° C. Certain aspects of the invention do not include cryogenic processing, e.g., cryogenic methane separation is not used.

The invention therefore particularly advantageous in remote or under-developed locations, where (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons.

The light paraffinic hydrocarbon feedstock is conducted to one or more reaction stages, where it is reacted in the presence of at least one catalyst for dehydrocyclization in at least one reaction zone operating under suitable dehydrocyclization conditions. The reaction converts at least a portion of the feedstock's light hydrocarbon to a product comprising aromatic hydrocarbon and in some embodiments molecular hydrogen. Certain aspects of the dehydrocyclization catalyst, its method of making and use in dehydrocyclization processes will now be described in more detail. The invention is not limited to these aspects, and this description is not meant to foreclose other aspects of the reaction stages within the broader scope of the invention.

Catalysts

In one aspect, the catalysts of this invention comprises a crystalline aluminosilicate zeolite having a constraint index of less than or equal to about 12, at least one metal selected from Group 3 to Group 13 of the IUPAC Periodic Table and phosphorous. In one or more embodiments, the catalyst contains at least about 0.005 wt. % of at least one metal, and 0.005 wt. % of phosphorous, preferably added phosphorous.

Typically the crystalline aluminosilicate zeolite is one having a medium pore size and a Constraint Index of less than or equal to about 12, preferably in the range of about 2 to 12. Constraint Index is defined in U.S. Pat. No. 4,016,218. Examples of suitable zeolites include ZSM-5, ZSM-11, ZSM-12, ZSM-21, ZSM-22, ZSM-23, ZSM-35, ZSM-38, and ZSM-48, including mixtures and intermediates thereof such as ZSM-5/ZSM-11 admixture. ZSM-5 is described in U.S. Pat. No. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. Zeolite ZSM-21 is described U.S. Pat. No. 4,082,805. ZSM-22 is described in U.S. Pat. No. 4,556,477. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is described in U.S. Pat. No. 4,234,231. TEA-Mordenite is described in U.S. Pat. Nos. 3,766,093 and 3,894,104. MCM-68 is described in U.S. Pat. No. 6,049,018.

Optionally, the zeolite is one comprising at least one set of pores of substantially uniform size extending through the molecular sieve, wherein geometric mean of the cross-sectional dimensions of each of the sets of pores is >5 Å, or >5.3 Å, e.g., ≥5.4 Å such as ≥5.5 Å, or in the range of 5 Å to 7 Å, or 5.4 Å to 7 Å.

Preferably, in one or more embodiments, the crystalline aluminosilicate zeolite having a constraint index of less than or equal to about 12 is selected from the group consisting of a MCM-22 family material, ZSM-5, ZSM-11, ZSM-12, ZSM-21, TEA-Mordenite, MCM-68 and mixtures of two or more thereof. Preferably, the aluminosilicate zeolite is ZSM-11 or H-ZSM-11 (the acidic form of ZSM-11), and more preferably, the aluminosilicate zeolite is ZSM-5 or H-ZSM-5 (the acidic form of ZSM-5).

In certain aspects, the molecular sieve has a relatively small crystal size, e.g., small crystal ZSM-5, meaning ZSM-5 having a crystal size ≤0.05 µm, such as in the range of 0.02 µm to 0.05 µm. Small crystal ZSM-5 and the method for determining molecular sieve crystal size are disclosed in U.S. Pat. No. 6,670,517, which is incorporated by reference herein in its entirety.

In other aspects, crystalline aluminosilicate zeolite comprises at least one molecular sieve of the MCM-22 family, e.g., MCM-22 alone or in combination with other aluminosilicates, specified above, or other MCM-22 family materials. Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), and ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve component. In one or more embodiments, the molecular sieve of the MCM-22 family is in the hydrogen form and having hydrogen ions, e.g., acidic.

The catalyst comprises a molecular sieve component, a metal component and phosphorous component. The molecular sieve component is preferably an aluminosilicate zeolite, in an amount of ≥20 wt. %, based on the weight of the catalyst, e.g., ≥25 wt. %, such as in the range of from 30 wt. % to 99.9 wt. %. In certain aspects, the molecular sieve component comprises aluminosilicate zeolite, e.g., ≥90 wt. % of at least one aluminosilicate zeolite. Although, the molecular sieve component may consist essentially of or even consist of zeolite, in alternative aspects the zeolite(s) is present in the molecular sieve component in combination with other (e.g., non-zeolitic) molecular sieve. The zeolite may be one that is in hydrogen form, e.g., one that has been synthesized in the alkali metal form, but is then converted from the alkali to the hydrogen form and having hydrogen ions, e.g., acidic.

In addition to the molecular sieve component, the catalyst comprises at least one metal component which is a metal selected from Group 3 to Group 13 of the IUPAC Periodic Table. The metal component may comprise one or more neutral metals selected from Groups 3 to 13 of the IUPAC Periodic Table, such as one or more of Ga, In, Zn, Cu, Re, Mo, W, La, Fe, Ag, Pt, and Pd, and/or a mixture of these metals. Preferably the metal is zinc, i.e., Zn.

The catalyst comprises from at least about 0.005 wt. %, or 0.01 wt. %, or 0.05 wt. %, or 0.10 wt. % up to about 1.0 wt. %, 2.0 wt. %, 3.0 wt. %, or 4.0 wt. %, or 5.0 wt. %, or 10.0 wt. % of the metal component, based on the weight of the catalyst. The catalyst may comprise from about 0.2 wt. % of the metal, such as ≥0.5 wt. % up to 1.0 wt. %, 2.0 wt. %, 3.0 wt. %, or 4.0 wt. %, or 5.0 wt. % of such metal. The metal componenent, based on the weight of the catalyst, is in the preferred range from at least about 1.0 wt. % up to about 5.0 wt. %, more preferably, in the range of at least about 0.005 up to about 3.0 wt. %. Those skilled in the art will appreciate that when the metal component comprises one or more metals of greater catalytic dehydrogenation activity, e.g., Pt, and/or Pd, a lesser amount of the metal component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the metal component comprises one or more metals of lesser dehydrogenation activity, e.g., one or more of Ga, In, Zn, Cu, Re, Mo, and W, a greater amount of the metal component is needed, e.g., in the range of 0.005 wt. % to 10 wt. %, based on the weight of the catalyst, such as 0.1 wt. % to 5 wt. %, or 0.5 wt. % to 2 wt. %.

The metal component may be provided on the catalyst in any manner, for example by conventional methods such as impregnation or ion exchange of the molecular sieve with a solution of a compound of the relevant metal.

In addition to the molecular sieve component and the metal component, the catalyst is modified by the addition of phosphorous, e.g., by impregnating phosphorous into molecular sieve. Conventional methods may be utilized to do so, but the invention is not limited thereto. The amount of added phosphorous is typically at least about 0.005 wt. %, or 0.01 wt. %, or 0.05 wt. %, or 0.10 wt. %, 0.2 wt. % up to about 1.0 wt. %, 2.0 wt. %, 3.0 wt. %, or 4.0 wt. %, or 5.0 wt. %, or 10.0 wt. % of phosphorous, based on the weight of the catalyst. Preferably the amount of phosphorous is 1.0 wt. %, based on the weight of the catalyst. In one or more embodiments, the phosphorous is deposited after the metal component has been deposited. Put another way, the phosphorous is deposited upon or proximate to the metal component, which is preferably, zinc.

Not to be bound by theory, it is believed that the deposition of phosphorous on the zinc-containing molecular sieve helps to retain the zinc on the molecular sieve component; particularly, in the process for dehydrocyclization of light paraffinic hydrocarbon feedstock of this invention. It is believed that when the molecular sieve component, such as for example, ZSM-5, is treated with a source of zinc, the zinc associates itself with the acid sites on the zeolite's pores and/or external surfaces. Thereafter, when the zinc-containing molecular sieve component is treated with a source of phosphorous, a zinc-phosphorus reaction occurs, thereby, improving the retention of the phosphorous on the molecular sieve component.

When the molecular sieve component comprises at least one aluminosilicate zeolite, e.g., at least one zeolite, the aluminosilicate zeolite's silica-to-alumina ($Si:Al_2$) atomic ratio is typically ≥2, e.g., in the range of from 5 to 100. The silica-to-alumina ratio, $Si:Al_2$, is meant to represent the $Si:Al_2$ atomic ratio in the rigid anionic framework of the crystalline aluminosilicate zeolite. In other words, aluminum in (i) any matrix or binder or (ii) in cationic or other form within the crystalline aluminosilicate zeolite's channels is excluded from the $Si:Al_2$ atomic ratio. Zeolite having a higher silica-to-alumina ratio can be utilized when a lower catalyst acidity is desired, e.g., in the range of from 44 to 100, such as from 50 to 80, or 55 to 75.

The catalyst of this invention provides an increased yield of single-ring aromatic hydrocarbon. In one or more embodiments, the catalyst provides a yield of single-ring aromatic hydrocarbon, of over 20 wt. %, preferably over 25 wt. %, under suitable dehydrocyclization conditions, preferably conditions which include at least a temperature of about 450° C. to about 650° C., a pressure of from about 35 kPa to about 1480 kPa and a WHSV from 0.1 to 20 $hr^{-1}$.

The catalyst of this invention forms a reduced amount of coke that is deposited on such catalyst during dehydrocyclization, as compared with conventional dehydrocyclization catalysts. In one or more embodiments, the catalyst provides a yield of coke of less than 5 wt. %, less than 10 wt. %, preferably less than 5 wt. %, of coke under suitable dehydrocyclization conditions, preferably conditions which include at least a temperature in the range of about 450° C. to about 650° C., a pressure of from about 35 kPa to about 1480 kPa and a WHSV from 0.1 to 20 $hr^{-1}$.

In one or more embodiments, the catalyst of this invention for the dehydrocyclization of a light paraffinic hydrocarbon feedstock comprising light $C_{5-}$ hydrocarbon to form single-ring aromatic hydrocarbon is made by any one of the methods disclosed hereinafter.

The invention is not limited to these aspects, and this description is not meant to foreclose other catalyst synthesis methods within the broader scope of the invention such as those using other molecular sieve components and/or other metal components and/or phosphorous.

Method of Making the Catalyst

Certain aspects of, the invention relate to a method of making one or more catalysts for use the dehydrocyclization of a light paraffinic hydrocarbon feedstock of this invention. The method comprising the steps of:

(a) contacting a crystalline aluminosilicate having a constraint index of less than or equal to about 12 with a source of said at least one metal selected from Group 3 to Group 13 of the IUPAC Periodic Table to form a metal-containing aluminosilicate having at least about 0.005 wt. % of said metal; and (b) then contacting said metal-containing aluminosilicate of step (a) with a source of phosphorus, whereby at least about 0.005 wt. % of phosphorus is deposited thereon, to form said catalyst.

In one or more embodiments, the metal-containing aluminosilicate comprises from at least about 0.005 wt. %, or 0.01 wt. %, or 0.05 wt. %, or 0.10 wt. % up to about 1.0 wt. %, 2.0 wt. %, 3.0 wt. %, or 4.0 wt. %, or 5.0 wt. %, or 10.0 wt. % of the metal, based on the weight of the catalyst.

The amount of phosphorous on the catalyst is typically at least about 0.005 wt. %, or 0.01 wt. %, or 0.05 wt. %, or 0.10 wt. %, 0.2 wt. % up to about 1.0 wt. %, 2.0 wt. %, 3.0 wt. %, or 4.0 wt. %, or 5.0 wt. %, or 10.0 wt. % of phosphorous, based on the weight of the catalyst. Preferably the amount of phosphorous is 1.0 wt. %.

Suitable sources of zinc are selected from the group consisting of zinc nitrate, zinc titanate, zinc silicate, zinc borate, zinc fluorosilicate, zinc fluorotitanate, zinc molybdate, zinc chromate, zinc tungstate, zinc zirconate, zinc chromite, zinc aluminate, zinc phosphate, zinc acetate dihydrate, diethyl zinc, zinc 2-ethylhexanoate, and mixtures of two or more thereof.

Suitable sources of phosphorous are selected from the group consisting of phosphorus oxide, phosphorus pentoxides, phosphorus oxychloride, phosphoric acid, phosphines, phosphites, phosphates, and mixtures of two or more thereof.

The catalyst can include the molecular sieve component in unbound or substantially binder-free form, that is, without a binder or matrix material. In particular, the catalyst can be substantially free of binder, e.g., contains ≤1 wt. % of binder, such as ≤0.1 wt. %. For example, the catalyst's molecular sieve component can comprises ≥95 wt. % of substantially binder-free bound molecular sieve, e.g., ≥95 wt. % of substantially binder-free ZSM-5, and in particular small crystal H-ZSM-5.

Alternatively, the molecular sieve component may be combined in a conventional manner with an oxide binder as hereinafter detailed. In a preferred embodiment, the molecular sieve component is in unbound or substantially binder-free form. In addition to the molecular sieve component and dehydrogenation component, the catalyst may further comprise an optional matrix component, e.g., one or more inorganic binders. A matrix component may be used, e.g., to make the catalyst more resistant to the temperatures and other conditions employed in the conversion reaction. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component may include active materials, such as synthetic or naturally occurring zeolites. Alternatively, or in addition, the matrix component may include clays and/or oxides such as alumina, silica, silica-alumina, zirconia, titania, magnesia or mixtures of these and other oxides. The matrix component may include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively or in addition, the matrix component may include one or more substantially inactive materials. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve thermal and strength properties (e.g., crush strength) of the catalyst under catalytic dehydrocyclization conditions. Alternatively or in addition to any phosphorous added to or impregnated into the molecular sieve component, the matrix component may optionally include phosphorous, e.g., to lessen catalyst acidity. Those skilled in the art will appreciate that lessening catalyst acidity decreases the amount of catalyst coke produced during the catalytic conversion of the feedstock's light hydrocarbon to aromatic hydrocarbon. Suitable phosphorous-containing matrices are disclosed in U.S. Pat. No. 5,026,937, which is incorporated by reference herein in its entirety.

Typically, the catalyst has a surface area in the range of from 100 m$^2$/g to 600 m$^2$/g, e.g., in the range of from 200 m$^2$/g to 500 m$^2$/g. The catalyst's acid cracking activity (alpha value) is typically ≤200, e.g., in the range of from 10 to 80. When the catalyst comprises aluminosilicate zeolite which includes phosphorous, the phosphorous:aluminum atomic ratio is typically in the range of from 0.01 to 0.5. For example, the catalyst may contain ≥10 wt. % of phosphorous-modified alumina, such as ≥15 wt. %, or in the range of from 10 wt. % to 20 wt. %.

Process

In still another aspect, the invention is a process for the dehydrocyclization of a light paraffinic hydrocarbon feedstock comprising one or more light hydrocarbons having no more than five carbon atoms to form a product comprising aromatic hydrocarbon having six or more carbon atoms, the process comprising the steps of contacting said feedstock under suitable conversion conditions in the presence of any one of the catalysts for dehydrocyclization of this invention to form said product.

One or more light hydrocarbons of the light paraffinic hydrocarbon feedstock having no more than five carbon atoms are selected from the group consisting of methane, ethane, propane, butane and mixtures of two or more thereof.

The aromatic hydrocarbon having six or more carbon atoms of the product are selected from the group consisting of benzene, toluene, xylenes and mixtures of two or more thereof.

Suitable dehydrocyclization conditions include at least a temperature in the range of about 450° C. to about 650° C., a pressure in the range of from about 35 kPa to about 1480 kPa and a WHSV from 0.1 to 20 hr$^{-1}$. In other embodiments, such conditions include a temperature in the range of from 400° C. to 630° C., and a pressure in the range of from about 138 kPa (20 psia) to about 2070 kPa (300 psia). Typically, the temperature is in the range of from 450° C. to 605° C., the pressure is in the range of from about 207 kPa (30 psia) to about 522 kPa (80 psia), and suitable dehydrocyclization conditions include a weight hourly space velocity (WHSV) in the range of from 0.1 to 10 hr$^{-1}$.

One or more reaction zones have one or more stages containing at least one bed of the specified catalyst. The catalyst may be in particulate form, as the dehydrocyclization reaction takes place as the feedstock traverses the catalyst bed. The catalyst bed may be one or more of a fixed, moving, or fluidized catalyst bed. It has been found that it is beneficial for the catalyst to have a residence time of ≤90 seconds in the dehydrocyclization reaction zone under dehydrocyclization conditions. It has been discovered that doing so dramatically increases the conversion of C$_{2+}$ hydrocarbon without a significant decrease in the selectivity for aromatic hydrocarbon, and without excessive selectivity for light hydrocarbon compounds such as methane. More particularly, it has been found that it is beneficial for the catalyst to have a residence time in the reaction zone under dehydrocyclization conditions of ≤60 seconds, e.g., ≤30 seconds, such as ≤10 seconds, or ≤1 second, or ≤0.1 second or in the range of from 0.001 second to 60 seconds. Especially when the catalyst is present in a moving bed and/or fluidized bed, it is beneficial for the catalyst to have a residence time in the dehydrocyclization reaction zone that is in the range of from 0.01 second to 10 seconds, e.g., 0.1 second to 10 seconds, such as 0.1 second to 1 second.

In one or more embodiments, the process further comprises a reaction zone for contacting said feedstock under said suitable conversion conditions in the presence of said catalyst, said reaction zone having a fixed catalyst bed disposed therein. In a fixed catalyst bed (also called a packed bed), the catalyst remains stationary in the reaction zone. The feedstock enters the first reaction zone proximate to the upstream end of a reactor. After the dehydrocyclization reaction is carried out in the bed, the product exits the first reaction zone near the downstream end of the reactor. The reaction zone within the reactor establishes a fixed reference frame, and the catalyst bed is "fixed" in the sense that it is substantially immobile with respect to the fixed reference frame during the dehydrocyclization reaction. The reactor may be, e.g., an adiabatic single bed, a multi-tube surrounded with heat exchange fluid or an adiabatic multi-bed with internal heat exchange, among others. At least one substantially similar second reaction zone may be operated in parallel with the first reaction zone, so that first reaction zone may be operated in reaction mode while the second reaction zone is operated in regeneration mode, to regenerate the second reaction zone's catalyst. Continuous or semi-continuous operation may be carried out by alternating reaction and regeneration modes in the first and second reaction zones.

In one or more embodiments, the process further comprising a reaction zone for contacting said feedstock under said suitable conversion conditions in the presence of said catalyst, said reactor zone having a moving or fluidized catalyst bed disposed therein. In a moving bed, particles of the specified catalyst flow under the influence of an external force such as gravity. The catalyst particles substantially maintain their relative positions to one another during the flow, resulting in a movement of the bed with respect to the fixed reference frame. Average flow of the specified feedstock with respect to the catalyst flow may be concurrent, countercurrent, or cross-current.

In a fluidized bed, a fluidizing medium (typically in the vapor phase) is conducted through the catalyst bed at a velocity sufficient to suspend the catalyst particles within the bed. The bed suspended catalyst particles typically has the appearance of a boiling fluid. The fluidizing medium's velocity is selected such that the fluidizing medium exerts a sufficient force on the catalyst particles to substantially balance the weight of the catalyst bed.

Conventional fixed, moving, and/or fluidized beds may be used in the first reaction zone, and optionally in the second reaction zone, but the invention is not limited thereto.

EXAMPLES

The invention will now be more particularly described with reference to the following Examples.

Six zinc-containing H-ZSM-5 catalysts were obtained. Approximately 1 wt. % of phosphorus (in the form of phosphoric acid) was added to three of these catalysts by incipient wetness impregnation. The other three catalysts did not contain phosphorous. These six catalysts were tested for the conversion of a model light paraffinic hydrocarbon feedstock which contained 46 vol. % of methane, 24 vol. % of ethane, 19 vol. % propane and 11 vol. % of $C_4$ alkanes). Table 2 shows the formulations of these catalysts.

TABLE 2

Samples tested for natural gas dehydrocyclization, both with and without the addition of 1 wt. % phosphorus

| Sample | Zeolite | Binder | Zeolite/Binder (wt./wt.) | Zinc Loading (wt. %) | Phosphorus Loading (wt. %) |
|---|---|---|---|---|---|
| A1 | H-ZSM-5 | Alumina (Versal 300) | 80/20 | 0.5 | 1 |
| A2 | H-ZSM-5 | Alumina (Versal 300) | 80/20 | 0.5 | 0 |
| B1 | H-ZSM-5 | None (substantially binder-free) | 100/0 | 0.5 | 1 |
| B2 | H-ZSM-5 | None (substantially binder-free) | 100/0 | 0.5 | 0 |
| C1 | H-ZSM-5 | None (substantially binder-free) | 100/0 | 1 | 1 |
| C2 | H-ZSM-5 | None (substantially binder-free) | 100/0 | 1 | 0 |

Figure 1A:
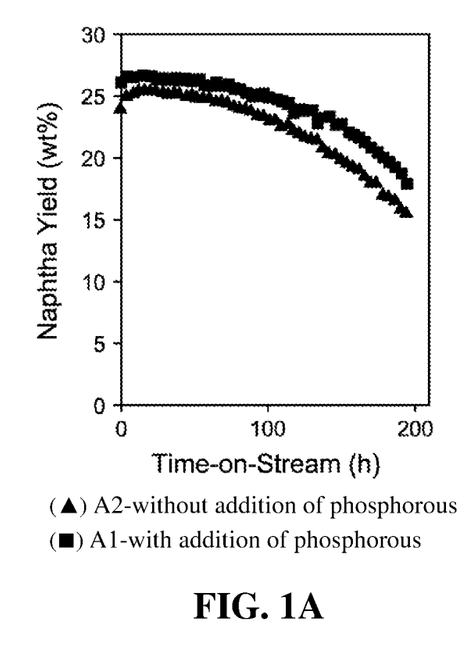
FIGS. 1A, 1B, and 1C are diagrams showing the yields of naphtha for the dehydrocyclization of a model light paraffinic hydrocarbon feedstock at 550° C., 0.5 WHSV and 1 kPa-g (1 barg) using the following catalysts investigated in the examples of this disclosure samples A1/A2, samples B1/B2, and samples C1/C2, respecitvely. The model light paraffinic hydrocarbon feedstock comprised 46 vol. % of methane, 24 vol. % of ethane, 19 vol. % of propane and 11 vol. % of $C_4$ alkanes was contacted with a zinc-containing ZSM-5 catalysts with and without the addition of phosphorus to form a product comprising naphtha along with non-aromatic hydrocarbon, molecular hydrogen, and unconverted light paraffinic hydrocarbon feedstock.
Figure 1B:
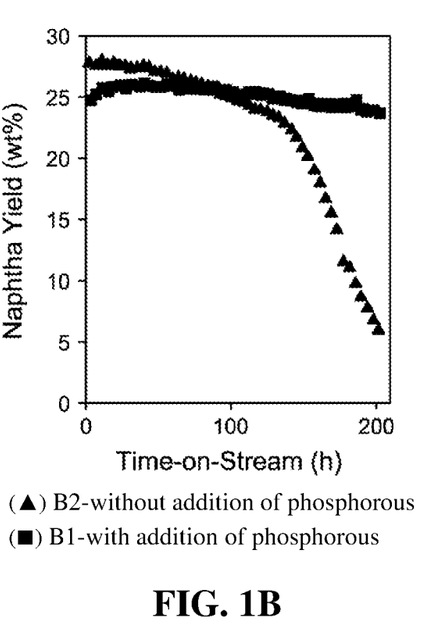
Figure 1C:
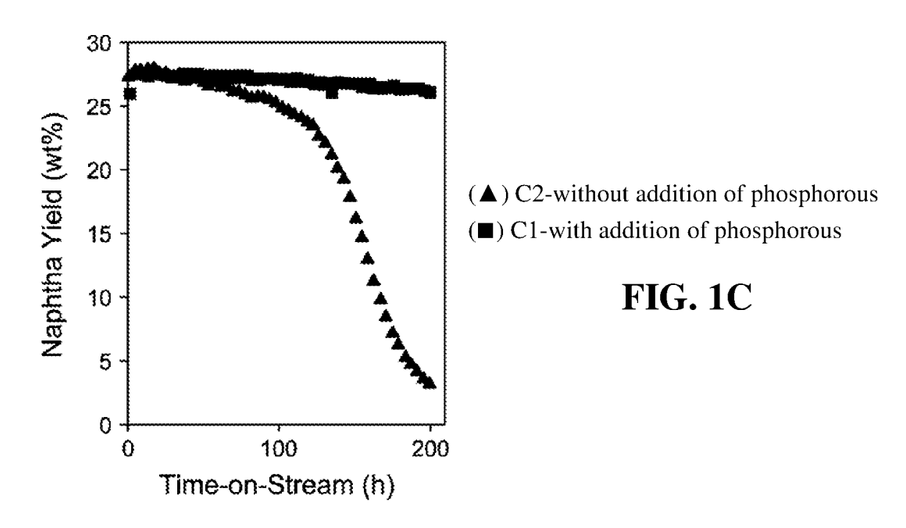

The effect of the addition of phosphorus on the yield of naphtha (as defined above) for the dehydrocyclization of a model light paraffinic hydrocarbon feedstock at 550° C., 0.5 WHSV and 1 kPa-g (1 barg) are shown in FIGS. 1A, 1B and 1C. The naphtha yields are maintained for a greater length of time for catalysts containing phosphorus as compared to the catalysts without phosphorus. The stabilization of the naphtha yields enables the catalyst cycle length to be increased by at least 25%.

FIGS. 1A, 1B, and 1C show that while all the catalysts in Table 2 benefit from the addition of phosphorus, the substantially binder-free catalysts (B1 and C1) are stabilized by phosphorus to a much greater extent than the alumina-bound catalyst (A1).

Figure 2:
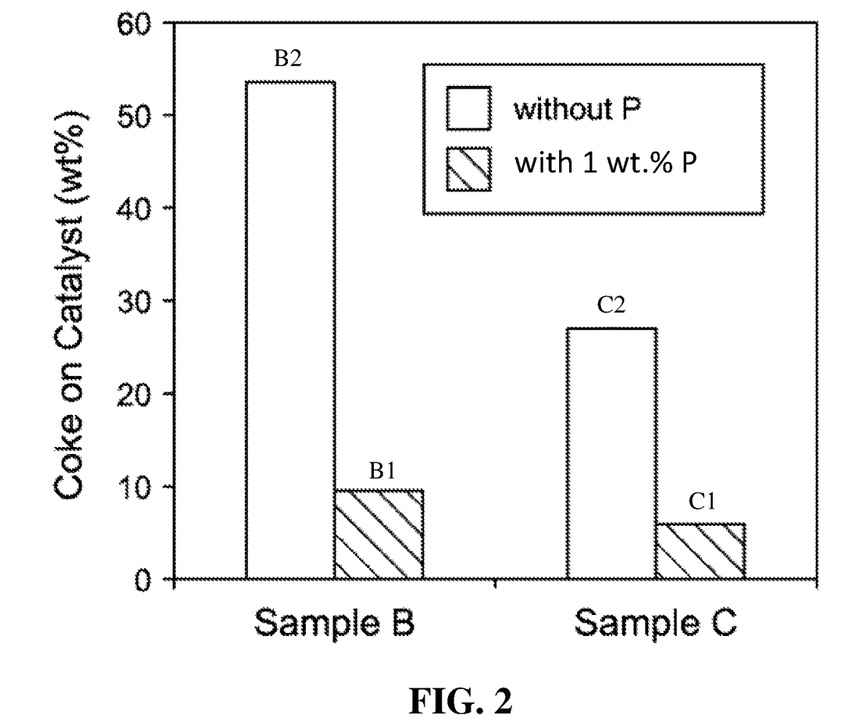
FIG. 2 is a diagram showing the amount of coke deposited on the catalysts investigated (B1, B2, C1, and C2) after 200 hours on stream in the dehydrocyclization of the above model light paraffinic hydrocarbon feedstock at 550° C., 0.5 WHSV and 1 kPa-g (1 barg).

FIG. 2 shows the amount of coke formed on the substantially binder-free catalysts without phosphorus (B2 and C2) and those with phosphorous (B1 and C1) after 200 hours of reaction (end of run). As may be seen, the results in FIG. 2 show that the addition of phosphorus to the substantially binder-free catalysts (B1 and C1) results in a significant decrease in the amount of coke formed. Further, FIG. 2 shows that the addition phosphorus increases the stability of the unbound catalyst B1 and C1 by suppressing the formation of coke.

Figure 3A:
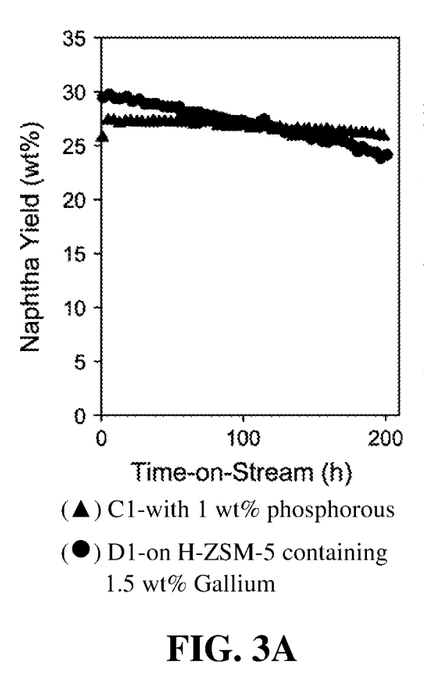
FIGS. 3A, 3B, and 3C are diagrams showing the naphtha yield, the propane conversion and the butane conversion, respectively, of the above model light paraffinic hydrocarbon feedstock at 550° C., 0.5 WHSV and 1 kPa-g (1 barg) as a comparison between the current invention, a substantially binder-free (Zn) H-ZSM-5 catalyst containing 1 wt. % phosphorus (Example C1), and a substantially binder-free H-ZSM-5 catalyst containing 1.5 wt. % gallium (Example D1).
Figure 3B:
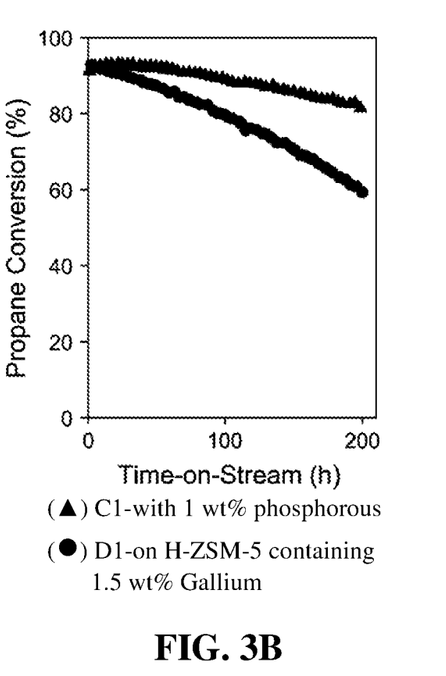
Figure 3C:
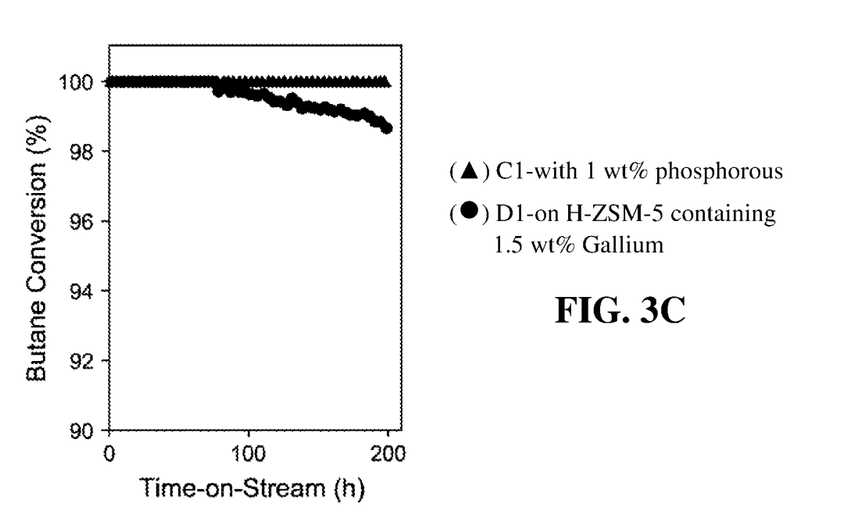

FIGS. 3A, 3B, and 3C show the naphtha yield, the propane conversion and the butane conversion, respectively, of the above model light paraffinic hydrocarbon feedstock at 550° C., 0.5 WHSV and 1 kPa-g (1 barg) as a comparison between the current invention, a substantially binder-free (Zn) H-ZSM-5 catalyst containing 1 wt. % phosphorus (C1) used in fixed bed applications, and a substantially binder-free H-ZSM-5 catalyst containing 1.5 wt. % gallium (D1) used in moving bed applications. As may be seen, the results in FIGS. 3A, 3B and 3C show that although the gallium-containing catalyst has higher initial naphtha yields from the model natural gas dehydrocyclization, the yield decreases from 30 wt. % to 24 wt. % over the course of 200 hours. In contrast, the current invention maintains naphtha yields between 26-27 wt. % for the same time period. Additionally, propane conversion and butane conversion is higher on the current invention compared to the gallium-containing catalyst. These results show that the current invention is more suitable for fixed bed applications than the current state-of-the-art catalyst, which is currently used in moving bed applications.

Certain embodiments and features have been described using a set of numerical upper limits and a set of numerical lower limits. When numerical lower limits and numerical upper limits are listed herein, ranges from any lower limit to any upper limit are contemplated, and are expressly within the scope of the invention. Certain lower limits, upper limits and ranges appear in one or more claims below. All numerical values take into account experimental error and variations that would be expected by a person having ordinary skill in the art. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group of consisting of," or "is" preceding the recitation of the composition, component, or components, and vice versa.

Various terms have been defined above. To the extent a term used in a claim is not defined above, it should be given the broadest definition persons in the pertinent art have given that term as reflected in at least one printed publication or issued patent. Furthermore, all patents, patent applications, any test procedures, and other documents cited in this application are fully incorporated by reference in their entirety to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The invention claimed is:

1. A process for the dehydrocyclization of a light paraffinic hydrocarbon feedstock comprising one or more light hydrocarbons having no more than five carbon atoms to form a product comprising aromatic hydrocarbon having six or more carbon atoms, the process comprising the steps of contacting said light paraffinic hydrocarbon feedstock under suitable dehydrocyclization conditions in the presence of at least one dehydrocyclization catalyst to form said product; wherein said dehydrocyclization catalyst is made by a method comprising the steps of:
(a) contacting a crystalline aluminosilicate zeolite having a constraint index of less than or equal to 12 with a source of at least one metal selected from Group 3 to Group 13 of the IUPAC Periodic Table to form a catalyst precursor comprising said aluminosilicate zeolite and at least 0.005 wt. % of said metal, based on the weight of the dehydrocyclization catalyst; and then
(b) contacting said catalyst precursor with a source of phosphorus and depositing at least 0.005 wt. % of phosphorus on said catalyst precursor, based on the weight of the dehydrocyclization catalyst, to form said dehydrocyclization catalyst,
wherein said catalyst is in substantially binder-free form.

2. The process of claim 1, wherein said one or more light hydrocarbons having no more than five carbon atoms are selected from the group consisting of methane, ethane, propane, butane and mixtures of two or more thereof.

3. The process of claim 1, wherein said aromatic hydrocarbon having six or more carbon atoms is selected from the group consisting of benzene, toluene, xylenes and mixtures of two or more thereof.

4. The process of claim 1, wherein said suitable dehydrocyclization conditions include at least a temperature in the range of 450° C. to 650° C., a pressure in the range of from 35 kPa to 1480 kPa and a WHSV from 0.1 to 20 hr$^{-1}$.

5. The process of claim 1, further comprising a reaction zone for contacting said light paraffinic hydrocarbon feedstock under said suitable dehydrocyclization conditions in the presence of said catalyst, said reaction zone having a fixed catalyst bed disposed therein.

6. The process of claim 1, further comprising a reaction zone for contacting said light paraffinic hydrocarbon feedstock under said suitable dehydrocyclization conditions in the presence of said catalyst, said reactor zone having a moving or fluidized catalyst bed disposed therein.

7. A process for the dehydrocyclization of a light paraffinic hydrocarbon feedstock comprising one or more light hydrocarbons having no more than five carbon atoms to form a product comprising aromatic hydrocarbon having six or more carbon atoms, the process comprising the steps of contacting said light paraffinic hydrocarbon feedstock under suitable dehydrocyclization conditions in the presence of at least one dehydrocyclization catalyst to form said product; wherein
said dehydrocyclization catalyst is made by a method comprising the steps of:
(a) contacting a crystalline aluminosilicate zeolite having a constraint index of less than or equal to 12 with a source of Zn to form a catalyst precursor comprising said aluminosilicate zeolite and at least 0.005 wt. % of Zn, based on the weight of the dehydrocyclization catalyst; and then
(b) contacting said catalyst precursor with a source of phosphorus and depositing at least 0.005 wt. % of phosphorus on said catalyst precursor, based on the weight of the dehydrocyclization catalyst, to form said dehydrocyclization catalyst,
wherein said catalyst is in substantially binder-free form.

8. The process of claim 1, wherein the catalyst precursor in (a) comprises at most 10 wt % of said metal.

9. The process of claim 8, wherein the catalyst precursor in (a) comprises at most 5 wt % of said metal.

10. The process of claim 9, wherein the catalyst precursor in (a) comprises at most 2 wt % of said metal.

11. The process of claim 8, wherein the catalyst precursor in (a) comprises at least 0.1 wt % of said metal.

12. The process of claim 11, wherein the catalyst precursor in (a) comprises at least 1.0 wt % of said metal.

13. The process of claim 9, wherein the catalyst precursor in (a) comprises at least 0.1 wt % of said metal.

14. The process of claim 13, wherein the catalyst precursor in (a) comprises at least 1.0 wt % of said metal.

15. The process of claim 10, wherein the catalyst precursor in (a) comprises at least 0.1 wt % of said metal.

16. The process of claim 15, wherein the catalyst precursor in (a) comprises at least 1.0 wt % of said metal.

17. The process of claim 1, wherein (b) comprises depositing at least 0.5 wt % of phosphorus on said catalyst precursor.

18. The process of claim 1, wherein (b) comprises depositing at least 1 wt % of phosphorus on said catalyst precursor.

19. The process of claim 17, wherein (b) comprises depositing at most 10 wt % of phosphorus on said catalyst precursor.

20. The process of claim 18, wherein (b) comprises depositing at most 10 wt % of phosphorus on said catalyst precursor.

21. The process of claim 7, wherein the catalyst precursor in (a) comprises at most 10 wt % of Zn.

22. The process of claim 21, wherein the catalyst precursor in (a) comprises at most 5 wt % of Zn.

23. The process of claim 22, wherein the catalyst precursor in (a) comprises at most 2 wt % of Zn.

24. The process of claim 7, wherein (b) comprises depositing at most 10 wt % of phosphorus on said catalyst precursor.

* * * * *